(12) United States Patent
Voipio

(10) Patent No.: US 9,719,919 B2
(45) Date of Patent: Aug. 1, 2017

(54) METHOD FOR MEASURING REFRACTIVE INDEX, AND REFRACTOMETER

(71) Applicant: Janesko Oy, Vantaa (FI)

(72) Inventor: Ville Voipio, Helsinki (FI)

(73) Assignee: JANESKO OY, Vantaa (FI)

( * ) Notice: Subject to any disclaimer, the term of this patent is extended or adjusted under 35 U.S.C. 154(b) by 376 days.

(21) Appl. No.: 14/162,083

(22) Filed: Jan. 23, 2014

(65) Prior Publication Data

US 2014/0268115 A1    Sep. 18, 2014

(30) Foreign Application Priority Data

Jan. 23, 2013  (FI) .................................. 20135064

(51) Int. Cl.
*G01N 21/43* (2006.01)
*G01N 21/41* (2006.01)
*G01J 3/50* (2006.01)
*G01N 21/03* (2006.01)
*G01N 21/25* (2006.01)
(Continued)

(52) U.S. Cl.
CPC ......... *G01N 21/4133* (2013.01); *G01N 21/43* (2013.01); *G01J 3/0205* (2013.01); *G01J 3/18* (2013.01); *G01J 3/502* (2013.01); *G01N 21/0303* (2013.01); *G01N 21/25* (2013.01); *G01N 2021/0389* (2013.01)

(58) Field of Classification Search
CPC ......... G01N 21/8483; G01N 2201/062; G01N 27/06
USPC .......... 356/128–136, 445, 328, 246, 491, 73
See application file for complete search history.

(56) References Cited

U.S. PATENT DOCUMENTS 3,628,867 A    12/1971  Brady
4,451,147 A    5/1984   Dobes et al.
(Continued)

FOREIGN PATENT DOCUMENTS

DE    102007039349 A1    2/2009
EP         0281337 A2    9/1988
(Continued)

OTHER PUBLICATIONS

Finnish Search Report mailed on Oct. 10, 2013 for Finnish Application No. 20135064.

*Primary Examiner* — Rebecca C Bryant
(74) *Attorney, Agent, or Firm* — Buchanan Ingersoll & Rooney PC

(57) ABSTRACT

An exemplary method for measuring a refractive index of a substance being measured through an optical window, includes arranging the optical window in contact with the substance being measured, directing light to the interface of the optical window and substance being measured, where part of the light is absorbed by the substance being measured and part of it is reflected from the substance being measured to form an image, in which the location of the boundary of light and dark areas expresses a critical angle of the total reflection dependent on the refractive index of the substance being measured, and examining the formed image. Light is directed on a first structure and to desired angles on an interface between the optical window and substance being measured. Light reflected from the interface of the optical window and substance being measured is directed on a second structure.

15 Claims, 4 Drawing Sheets

(51) Int. Cl.
*G01J 3/02* (2006.01)
*G01J 3/18* (2006.01)

(56) References Cited

U.S. PATENT DOCUMENTS

| | | | |
|---|---|---|---|
| 4,569,590 A * | 2/1986 | Karny | G01N 21/41 |
| | | | 356/128 |
| 4,571,075 A | 2/1986 | Kamrat | |
| 4,962,746 A | 10/1990 | Miyata et al. | |
| 5,082,629 A | 1/1992 | Burgess, Jr. et al. | |
| 5,083,018 A | 1/1992 | Rhyne | |
| 5,396,325 A | 3/1995 | Carome et al. | |
| 5,694,210 A | 12/1997 | Newell et al. | |
| 5,742,382 A | 4/1998 | Kahre | |
| 6,108,083 A * | 8/2000 | Machler | G01J 3/02 |
| | | | 356/246 |
| 6,760,098 B2 | 7/2004 | Salo | |
| 8,934,102 B2 * | 1/2015 | Wirthlin | G01N 21/43 |
| | | | 356/448 |
| 2003/0193662 A1 * | 10/2003 | DiFoggio | G01N 21/41 |
| | | | 356/128 |
| 2005/0063869 A1 * | 3/2005 | Follonier | G01N 21/0303 |
| | | | 422/82.05 |
| 2006/0012776 A1 | 1/2006 | Newell et al. | |
| 2010/0020423 A1 * | 1/2010 | Phillips | G02B 26/06 |
| | | | 359/846 |
| 2010/0233329 A1 * | 9/2010 | Marno | G01N 21/359 |
| | | | 426/231 |
| 2014/0332674 A1 * | 11/2014 | Goto | G01N 30/74 |
| | | | 250/227.11 |

FOREIGN PATENT DOCUMENTS

| | | |
|---|---|---|
| EP | 0359167 A2 | 3/1990 |
| EP | 0836092 A2 | 4/1998 |
| FI | 65496 C | 5/1984 |
| FI | 96451 | 3/1996 |
| GB | 2014724 A | 8/1979 |

\* cited by examiner

METHOD FOR MEASURING REFRACTIVE INDEX, AND REFRACTOMETER

RELATED APPLICATION(S)

This application claims priority under 35 U.S.C. §119 to Finnish application 20135064 filed in Finland on Jan. 23, 2013, the entire content of which is hereby incorporated by reference in its entirety.

FIELD

The present disclosure relates to a method for measuring a refractive index of a substance being measured through an optical window.

BACKGROUND INFORMATION

It is known in the art to define the refractive index of a material by means of the critical angle of the total reflection. In the measuring method, the critical angle of the total reflection of light is measured at the interface of the optical window, so-called measuring window, and the substance being measured, such as liquid. The refractive index being measured is then obtained by means of the Snell law $$n = n_i \sin \alpha_c. \quad (1)$$

In equation (1), n is the refractive index of the substance, such as liquid, being measured, $n_i$ is the refractive index of the material of the measuring window and $\alpha_c$ is the critical angle of the total reflection. According to an exemplary embodiment, the refractive index of the measuring window should be bigger than the refractive index of the substance being measured.

It is also known in the field to have the critical angle of the total reflection express as a boundary of light and dark areas by directing the light reflected from the interface of the window and liquid by means of a lens system to a cell of an image detector, such as camera.

In known designs, the lens system can be set to be at a distance equal to its focal length from the camera. Refractometers, in which light is directed through prism-like surfaces to the interface of the liquid being measured and measuring window, are also known components. Prism-like surfaces are always oblique in relation to the interface.

Liquids to be measured in different processes can be pressurized. Therefore, the measuring window should be sealed to prevent the liquid being measured from entering the measuring device. To achieve good pressure resistance, the sealing can be done in such a manner that the pressure directed to the measuring window presses the seal against the frame part of the measuring device. Oblique prism-like surfaces used in measuring windows of known systems can complicate the sealing of the measuring window. For example, using a known oblique prism-like structure can make it difficult to obtain a structure in which the process pressure would press the seal to be tighter.

Many prism-like solutions based on surfaces that are oblique in relation to the measuring surface are known in the art. Examples of known solutions are described in publications U.S. Pat. No. 4,451,147, EP 0 359 167 A3, U.S. Pat. No. 3,628,867, GB 2014724, FI 65496, FI 96451, U.S. Pat. No. 6,760,098, EP 0 836 092, EP 0 281 337 and U.S. Pat. No. 4,962,746.

SUMMARY

An exemplary method for measuring a refractive index of a substance being measured through an optical window is disclosed, the method comprising: arranging the optical window in contact with the substance being measured; directing light from a light source at a distance from the optical window to an interface of the optical window and substance being measured, wherein a first part of the light is absorbed by the substance being measured and a second part of the light is reflected from the substance being measured to form an image having light and dark areas; and examining the image by directing light from the light source to a first structure, which is formed on a surface of the optical window facing away from the substance being measured and is on the order of magnitude of the wavelength of light, and with which the light is directed to desired angles on the interface between the optical window and substance being measured, and the light reflected from the interface between the optical window and substance being measured is directed to a second structure which is formed on a surface of the optical window facing away from the from the substance being measured and is on the order of magnitude of the wavelength of light, and with which the light is directed for analysis.

An exemplary refractometer for measuring a refractive index from liquid I s disclosed, the refractometer comprising: an optical window that that has a surface in contact with a substance being measured and a parallel surface that faces away from the substance being measured; a light source disposed at a distance from the optical window and a beam of light rays to be emitted and directed to the surface of the optical window that faces away from the substance being measured; a first structure for directing the beam of rays to an interface between the optical window and substance being measured, whereby a first part of the beam of rays is absorbed by the substance being measured and a second part of the beam is reflected back from the substance being measured and forms an image having which a boundary of light and dark areas; an image detector at a distance from the optical window for examining the formed image; and a second structure that is arranged to direct the reflected part of the image to the image detector for analysis, wherein the first and second structures are formed on a front surface of the optical window facing away from the substance being measured, and at least one of the first and second structures are structures on the order of magnitude of the wavelength of light.

BRIEF DESCRIPTION OF THE DRAWINGS

The disclosure will be explained in the following in more detail by means of working examples described in the attached drawing, in which.

DETAILED DESCRIPTION

Exemplary embodiments of the present disclosure provide a method and a measuring device, with which the prior-art drawbacks can be eliminated by directing light to a first structure which is formed on a surface of the optical window facing away from the substance being measured and with which the light is directed to desired angles on the interface between the optical window and substance being measured, and by directing the light reflected from the interface of the optical window and substance being measured to a second structure which is formed on a surface of the optical window facing away from the substance being measured and with which the light is directed for analysis. The refractometer of the exemplary embodiments described herein is, in turn, where the first and second structures are formed on a front surface of the optical window facing away from the substance being measured.

Further exemplary embodiments of the present disclosure provide that the oblique surfaces of the optical window that have been problematic for the sealing of the window are eliminated. The optical window can press against a support surface on the frame part of the device under the effect of the substance being measured, whereby the seal arranged between the window and the above-mentioned support surface and, therefore, the sealing of the entire window works in a suitable manner. Exemplary embodiments also provide simplicity which results from the elimination of the many divergent polished surfaces used in known designs, for example.

As stated above, problem areas of known designs relate to the oblique prism-like surfaces of the optical window. According to an exemplary embodiment of the present disclosure, the measuring window can be formed such that it does not call for optical surfaces that are oblique in relation to the surface of the optical window which is in contact with the substance being measured. The surface of the optical window in contact with the substance being measured and the surface of the optical window facing away from the substance being measured can be parallel surfaces. Thus, there are no oblique optically active surfaces. The above-mentioned detail is clearly shown in the Figures. This property facilitates the provision of good sealing.

Figure 1:
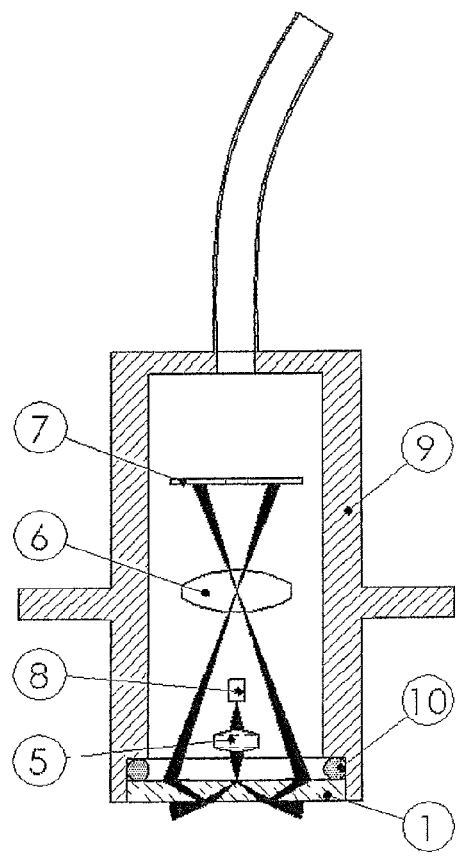
FIG. 1 illustrates a side projection of a measuring device in accordance with an exemplary embodiment of the present disclosure.
Figure 2:
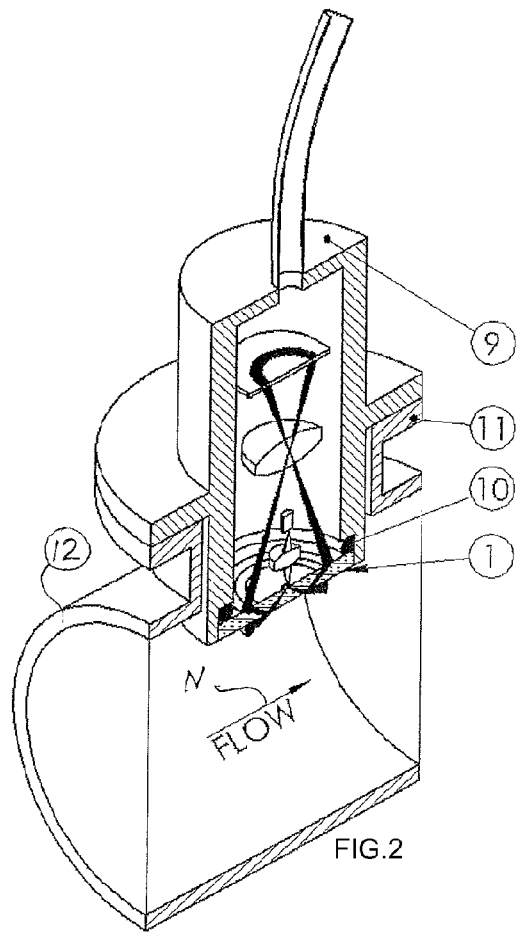
FIG. 2 shows a measuring device installed in a process pipe in accordance with an exemplary embodiment of the present disclosure.

FIG. 1 illustrates a side projection of a measuring device in accordance with an exemplary embodiment of the present disclosure. FIG. 2 shows a measuring device installed in a process pipe in accordance with an exemplary embodiment of the present disclosure. FIGS. 1 and 2 show a cross-section inside an exemplary an measuring device of the present disclosure, and the measuring device installed using a flange joint 11 in a process pipe 12.

FIGS. 1 and 2 also show an exemplary sealing solution described further herein. In the Figures, the detail indicated by reference number 10 is a known sealing. In this context, it should be understood that the sealing may be any known sealing, such as a normal O-ring.

The optical window 1, or measuring window, presses the O-ring against the frame part 9 of the device under the pressure of the substance being measured. The substance being measured is shown in principle with an arrow in FIG. 2. As shown in FIG. 2, the substance being measured flows under pressure in a process pipe 12. The term substance being measured should in this context be understood broadly, e.g., the term can cover all possible liquids and solutions used in various processes. The substance being measured can also be a solid substance that is in medium-free contact with the optical window. This type of solid substance may be a gem material, mineral or an optical material, for example.

In FIG. 2, the process pipe 12 is a pipe, in which the substance, e.g., a liquid, being measured flows. The term process pipe should, however, be understood broadly in this context, in other words, to cover even the container, in which the liquid is, or other suitable structure as desired.

Installing the measuring device in the process pipe and the structure and operation of the measuring device can be achieved through known technology and processes such that they are not presented in any greater detail.

Figure 3:
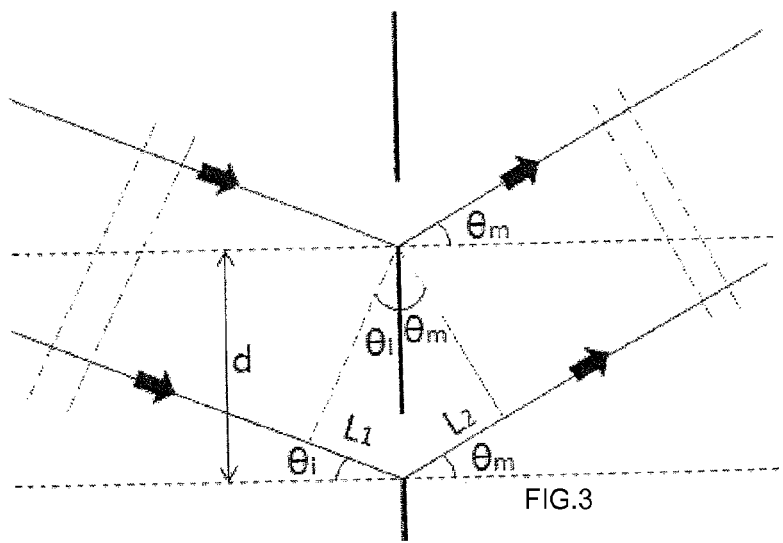
FIG. 3 is a view illustrating the travel of light in a diffractive structure, when the light arrives at a certain angle in accordance with an exemplary embodiment of the present disclosure.

FIG. 3 is a view illustrating the travel of light in a diffractive structure, when the light arrives at a certain angle in accordance with an exemplary embodiment of the present disclosure.

According to an exemplary embodiment of the present disclosure, the light specified in measuring the refractive index is, instead of the oblique prism-like surfaces used in known systems, directed to a structure that is on the surface of the measuring window, e.g., the surface of the measuring window facing away from the substance being measured, and that directs the light into desired measuring angles, and to a second structure that directs the light for analysis. The optical window (e.g., measuring window) can be made of any suitable material. Examples of suitable materials are mineral materials, such as sapphire.

The structures on the surface of the measuring window are structures that are on the order of magnitude of the wavelength of light and designed to refract light in a desired manner. The refractive property can be achieved by a diffractive structure or the like. A diffractive structure can be made on the surface of the measuring window by producing a mask of the desired structure on the surface and removing material from the areas free of the mask by an ion beam or by etching. At a basic level, the diffractive structure may be a diffraction lattice, for example. The lattice should be made in a manner such that the first diffraction maximum is at a desired angle to the normal of the measuring window. The angle can be selected so that it corresponds to the critical angle of the total reflection that is obtained in the center point of the measuring area of the refractive index.

Diffractive structures can be made directly on the surface of the optical window material, as stated above. However, it is also possible to make the diffractive structures on a coating arranged on the surface of the optical window. Titan oxide (TiO2), for example, may be used as the coating. The thickness of the coating is in the order of magnitude of wavelength, yet below it.

Diffractive structures can also be made in both the optical window material and coating.

In a diffractive structure, such as diffraction lattice, a maximum is formed at an angle, at which a constructive interference is obtained from adjacent lattice openings. Light waves join constructively, when light that has passed through different openings is cophasal. Cophasality occurs at certain angles to the normal of the lattice. At these angles, the difference in travel of light passed through adjacent openings is a multiple of the wavelength. For light arriving perpendicularly to the diffraction lattice, the angles θm of maximum intensity are determined by the distance d between the lattice openings and the wavelength λ of the used light in accordance with the equation $$d \sin \theta_m = m\lambda. \quad (2)$$

In equation (2), m is an integer, which is one for the first order maximum. A sufficient angular distribution for the measurement is obtained around the maximum by directing light to the lattice at different angles.

FIG. 3 is a schematic representation of the situation of light arriving at an angle θi. In FIG. 3, the medium is assumed to be air on both sides of the lattice. Here, too, the maximum of intensity is obtained at an angle, at which light waves join constructively. This occurs, when the distance of travel $L_1+L_2$ for light traveling through adjacent openings is a multiple of the wavelength.

Angle $\theta_i$ is positive, if it is on the same side of the axis as angle $\theta_m$ and negative on the opposite side. Thus, for light arriving at angle $\theta_i$, the equation (2) changes into the form $$d(\sin \theta_i + \sin \theta_m) = m\lambda. \quad (3)$$

From this equation, the angle $\theta_m$ of maximum intensity for light arriving at angle $\theta_i$ can be solved with equation (4)

$$\theta_m = \arcsin\left(\frac{m\lambda}{d} - \sin\theta_i\right). \quad (4)$$

When the material on the other side of the lattice is other than air, the distance $L_2$ should be transformed into an optical distance by multiplying it with the refractive index of the medium. If the refractive index of the measuring window is $n_s$, equation (4) is transformed into $$\theta_m = \arcsin\left(\frac{m\lambda}{dn_s} - \frac{1}{n_s}\sin\theta_i\right). \quad (5)$$

Figure 4A:
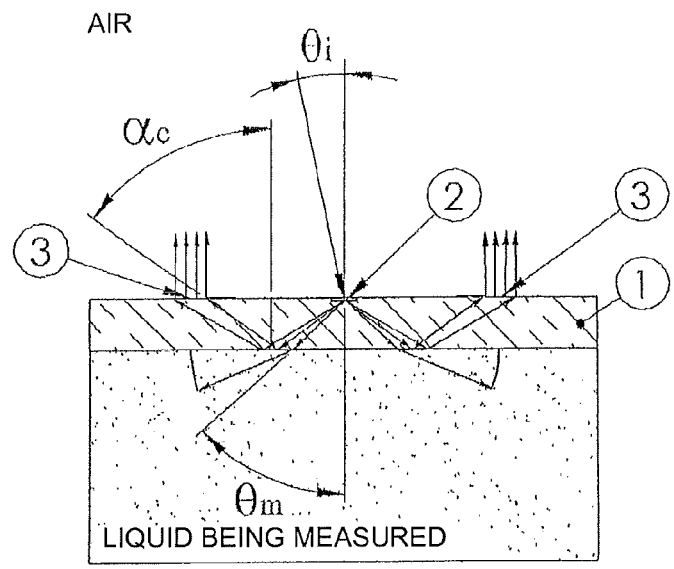
FIG. 4a is a view illustrating an optical measuring window in accordance with an exemplary embodiment of the present disclosure.

FIG. 4a is a view illustrating an optical measuring window in accordance with an exemplary embodiment of the present disclosure. FIG. 4a shows angles $\theta_i$ and $\theta_m$ placed into the measuring window. Angle $\theta_m$ and thus also angle $\theta_i$ should be selected to correspond to the critical angle of the total reflection on the top and bottom limits of the refractive index measurement area. This way, light is received on the interface of the measuring window at all the angles, the refractive indexes of which should be measured. In FIG. 4a, the angles are shown on the bottom limit of the measurement area. In FIG. 4a, the refractive index of the substance being measured, for instance liquid, is selected to be approximately in the middle of the measurement area. FIG. 4a also shows both the totally reflected part of light and the part of light that has refracted to the liquid.

Figure 4B:
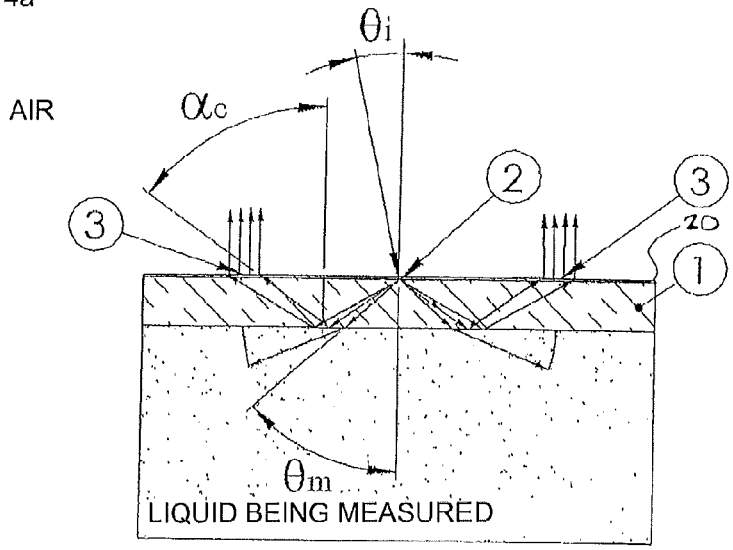
FIG. 4b illustrates a measuring device having light-directing structures formed on a coating in accordance with an exemplary embodiment of the present disclosure.
Figures 5, 6:
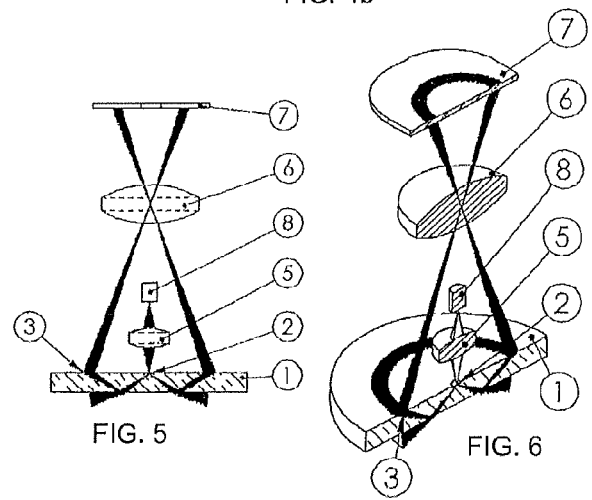
FIG. 5 illustrates optical parts of the measuring device of FIG. 4a in accordance with an exemplary embodiment of the present disclosure.
FIG. 6 illustrates a measuring device in which the critical angle is expressed as a torus in accordance with an exemplary embodiment of the present disclosure.

In the following, the disclosure will be described in greater detail by means of FIGS. 4a, 4b and 5. FIG. 4b illustrates a measuring device having light-directing structures formed on a coating in accordance with an exemplary embodiment of the present disclosure. FIG. 5 illustrates optical parts of the measuring device of FIG. 4a in accordance with an exemplary embodiment of the present disclosure.

It should be understood that the exemplary embodiments shown in FIGS. 4a and 4b have comparable functionality.

FIGS. 4a, 4a and 5 are perspective views of an optical window, e.g., measuring window 1, and its operation as well as other components related to measurement.

According to an exemplary embodiment of the present disclosure, the light source may be a suitable monochromatic light source, for example a laser diode 8 that is at a distance from the optical window 1. From the light source, the light is brought to the first structure 2 on the measuring window 1 by means of suitable lens optics 5, for instance.

Light refracts from the first structure 2 on the surface of the optical window to desired angles on the interface of the optical window 1 and substance being measured. On the interface, total reflection takes place for part of the light and part of it refracts to the liquid being measured. Total reflection takes place at larger angles than a given critical angle $\alpha_c$. Totally reflected light travels back to the opposite surface of the measuring window, in other words, back to the surface of the optical window that faces away from the substance being measured. This surface has the second structure 3.

The first structure 2 and the second structure 3 may have diffractive structures, for example.

The above-mentioned structures may be made to direct light in a desired manner. For instance, the second structure 3 can be formed to direct light for analysis at a suitable image detector, such as image detector/camera 7. An image is then formed in the camera, in which the critical angle $\alpha_c$ of the total reflection is expressed as a boundary of light and dark areas. For instance, the directing structure may be one that acts as a lens and directs parallel beams to the same point on the image detector 7. When the structure 3 has the above-mentioned directing property, the structure 2 may also be a diffusing or fluorescent structure. When the structure 3 has a directing property, lens structures 6 can be omitted. If the structure 2 is a diffusing or fluorescent structure, the dimensional accuracy of the refractive index depends on the size of the light point on the structure 2.

The second structure 3 may also be a diffusing or fluorescent structure. The critical angle of the total reflection is then expressed as a boundary of light and dark areas on the structure located on the surface of the window. Lens structures 6 that form an image of the boundary of light and dark areas on the image detector can be arranged between the structure 3 and camera/image detector 7.

In another exemplary embodiment described herein, both structures 2 and 3 can be diffusive or fluorescent structures.

FIG. 6 illustrates a measuring device in which the critical angle is expressed as a torus in accordance with an exemplary embodiment of the present disclosure. It is advantageous for the measurement that the boundary between the light and dark areas is easily analyzable by known image analysis means. An advantageous analysis form for this boundary is a circle. The light then should radiate from the structure 2 around the axis of the window. This type of situation is shown as cross-sectional view in FIG. 6. The inner diameter of the torus formed by light on the surface of the measuring window is then the expression of the critical angle being measured. The inner diameter of the circle is measured for instance by taking a picture of it with the camera 7 and by analyzing this camera image by using known image analysis techniques. In this situation, the first structure 2 is more complex than in the case of a simple lattice. However, the diffractive structure radiating around the axis of the measuring window 1 can be determined by calculative means by using the Maxwell equations, for example.

Figure 7:
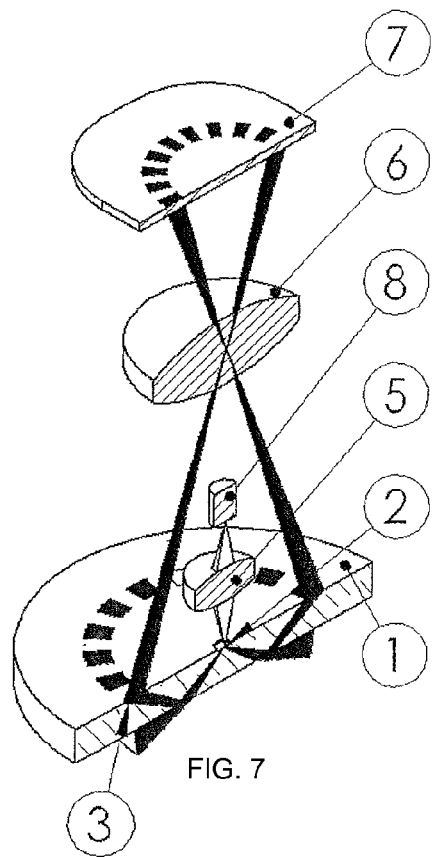
FIG. 7 illustrates a measuring device in which the critical angle is expressed as an inner diameter of sectors in accordance with an exemplary embodiment of the present disclosure.

FIG. 7 illustrates a measuring device in which the critical angle is expressed as an inner diameter of sectors in accordance with an exemplary embodiment of the present disclosure. As shown in FIG. 7, the illuminated areas formed on the surface of the measuring window 1 are circle sectors. According to an exemplary embodiment, the critical angle can be expressed as the inner diameter of the sectors. This situation arises, when light radiates a point pattern from the first structure 2 around the axis of the measuring window 1 to certain angles.

Figure 8:
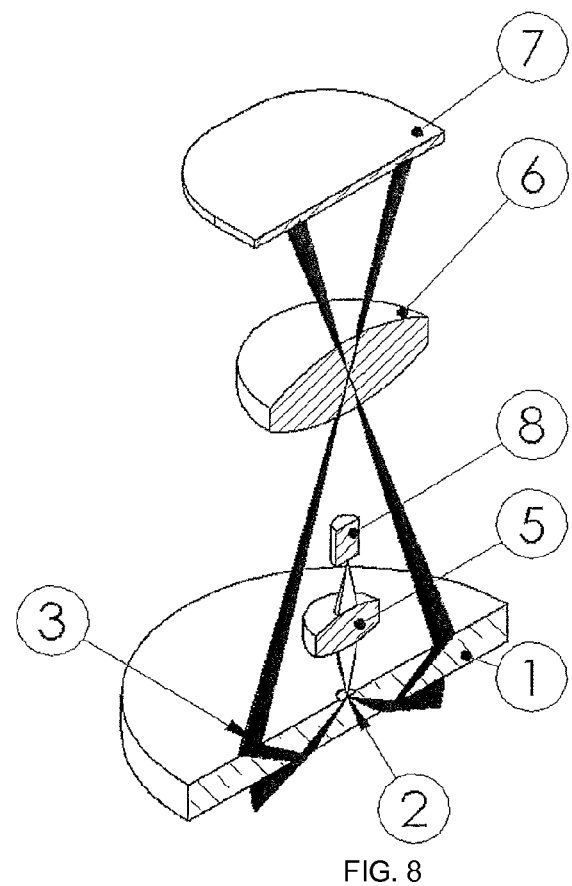
FIG. 8 illustrates a measuring device in which the critical angle is expressed as a distance of the innermost point of the line-like areas from the center point of the optical measuring window in accordance with an exemplary embodiment of the present disclosure.

FIG. 8 illustrates a measuring device in which the critical angle is expressed as a distance of the innermost point of the line-like areas from the center point of the optical measuring window in accordance with an exemplary embodiment of the present disclosure. FIG. 8 shows an exemplary embodiment in which the illuminated areas formed on the surface of the measuring window 1 are line-shaped. In this case, the critical angle is expressed as the distance of the innermost point of the lines from the center point of the measuring window 1. This situation arises, when the first structure 2 radiates light to two points in opposite directions and the light arriving at the first structure 2 has a narrow angular distribution with respect to the measuring direction in the perpendicular direction.

FIGS. 5 to 8 illustrate exemplary embodiments in which the arrangement formed by the first and second structures 2, 3 is symmetric in relation to the center point of the optical window. However, this is not the only possible solution, and according to other exemplary embodiments of the present disclosure, it can be possible to position the first and second structures 2, 3 otherwise, in other words, outside the center point of the optical window in such a manner that both the first and second structure 2, 3 is positioned offset from the center point of the optical window.

Figure 9:
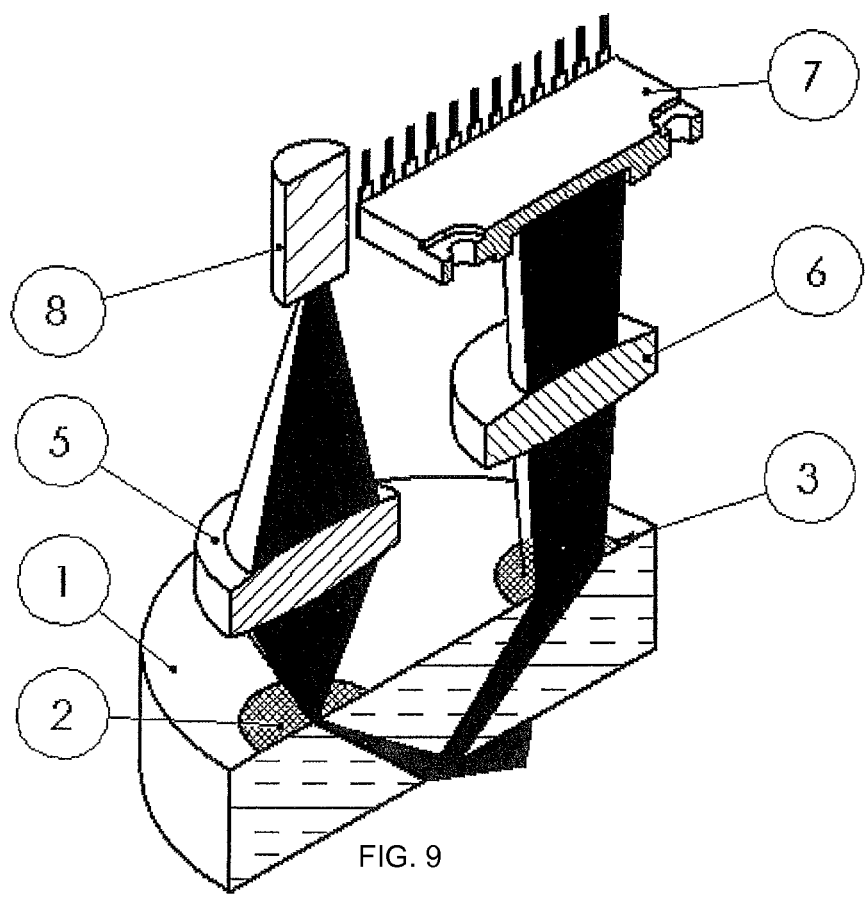
FIG. 9 illustrates a measuring device in which structures on the surface of the optical window are outside the center point of the optical measuring window in accordance with an exemplary embodiment of the present disclosure.

FIG. 9 illustrates a measuring device in which structures on the surface of the optical window are outside the center point of the optical measuring window in accordance with an exemplary embodiment of the present disclosure.

As shown in FIG. 9, the first structure 2 and the second structure 3 are positioned side by side on the surface of the optical window that faces away from the substance being measured. In operation, the exemplary embodiment of FIG. 9 corresponds to the exemplary embodiments of FIGS. 5 to 8 already described.

The same reference numbers are used in all Figures to indicate corresponding details.

The above working examples are not intended to limit the disclosure in any way, but the disclosure may be varied freely within the scope of the claims. Therefore, it should be understood that the refractometer as described in the present disclosure is not limited to the features shown in the Figures, and solutions of other type are also possible. The Figures should be seen only as representative Figures and not as Figures showing detailed structures.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for measuring a refractive index of a substance being measured through an optical window, the method comprising:
    arranging the optical window of a measuring device in contact with the substance being measured;
    directing light from a light source normal to a flow direction of the substance being measured and at a distance from the optical window to an interface of the optical window and the substance being measured, wherein a first part of the light is absorbed by the substance being measured and a second part of the light is reflected from the substance being measured to form an image having light and dark areas; and
    examining the image by directing light from the light source to a first structure, which is formed on a surface of the optical window facing away from the substance being measured and has a size on the order of magnitude of the wavelength of light, and with which the light is directed to desired angles on the interface between the optical window and substance being measured, and the light reflected from the interface between the optical window and substance being measured is directed to a second structure which is formed on a surface of the optical window facing away from the substance being measured and is on the order of magnitude of the wavelength of light, and with which the light is directed for analysis.

2. The method as claimed in claim 1, wherein the light-refracting property of at least one of the first and second structure is provided by a diffractive structure.

3. The method as claimed in claim 2, including:
    generating a beam of light rays via the first structure, which is configured or arranged to refract the beam around the normal of the optical window in such a manner that light reflected from the interface of the optical window and the substance being measured forms on the surface of the optical window facing away from the substance being measured, the beam forming a circular pattern, sector-like circular pattern or pattern formed by line-like areas, and wherein the inner diameter of the patterns or the distances between inner edges of opposite sectors/lines form a boundary of light and dark areas that expresses a critical angle of the total reflection.

4. The method as claimed in claim 1, including:
    generating a beam of light rays is generated via the first structure, which is configured or arranged to refract around the normal of the optical window in such a manner that light reflected from the interface of the optical window and substance being measured forms on the surface of the optical window facing away from the substance being measured, the beam forming a circular pattern, sector-like circular pattern or pattern formed by line-like areas, and wherein the inner diameter of the patterns or the distances between inner edges of opposite sectors/lines form a boundary of light and dark areas that expresses a critical angle of the total reflection.

5. The method as claimed in claim 1, wherein a location of a boundary between light and dark areas expresses a critical angle of the total reflection dependent on the refractive index of the substance being measured.

6. A refractometer for measuring a refractive index from a substance, the refractometer comprising:
- an optical window that has a surface in contact with a substance being measured and a parallel surface that faces away from the substance being measured;
- a light source disposed at a distance from the optical window and a beam of light rays to be emitted and directed normal to a flow direction of the substance being measured and directed to the surface of the optical window that faces away from the substance being measured;
- a first structure for directing the beam of rays to an interface between the optical window and substance being measured, whereby a first part of the beam of rays is absorbed by the substance being measured and a second part of the beam is reflected back from the substance being measured and forms an image having which a boundary of light and dark areas;
- an image detector at a distance from the optical window for examining the formed image; and
- a second structure that is arranged to direct the reflected part of the image to the image detector for analysis,
- wherein the first and second structures are formed on a front surface of the optical window facing away from the substance being measured, and at least one of the first and second structures has a size on the order of magnitude of the wavelength of light.

7. The refractometer as claimed in claim 6, wherein at least one of the first and second structures is a diffractive structure.

8. The refractometer as claimed in claim 6, wherein the at least one first and second structure is a diffraction lattice, a first diffraction maximum of which is at a desired angle to a normal of the optical window.

9. The refractometer as claimed in claim 8, wherein the angle is selected to generate a critical angle of the total reflection that is obtained at a center point of the measuring area of the refractive index.

10. The refractometer as claimed in claim 6, wherein the first and second structures are made on at least one of the production material of the optical window and a coating arranged on the surface of the production material of the optical window.

11. The refractometer as claimed in claim 10, wherein at least one of the first and second structure is a diffractive structure.

12. The refractometer as claimed in claim 6, wherein the first and second structures are arranged symmetrically in relation to a center point of the optical window.

13. The refractometer as claimed in claim 6, wherein the first and second structures are arranged outside a center point of the optical window.

14. The refractometer as claimed in claim 6, wherein the light and dark areas expresses a critical angle of the total reflection dependent on a refractive index of the substance being measured.

15. A method for measuring a refractive index of a substance being measured through an optical window using a refractometer as claimed in claim 5, including:
- directing a beam of light rays around a normal of the optical window via the first structure such that light reflected from an interface of the optical window and the substance being measured forms, on the surface of the optical window facing away from the substance being measured, a circular pattern, a sector-like circular pattern, or a pattern formed by line-like areas, and wherein an inner diameter of the patterns or distances between inner edges of opposite sectors/lines form a boundary of light and dark areas that expresses a critical angle of the total reflection.

* * * * *